(12) United States Patent
Liu et al.

(10) Patent No.: US 12,215,358 B1
(45) Date of Patent: Feb. 4, 2025

(54) COXSACKIEVIRUS A6 STRAIN CVA6-KM-J33 AND USE THEREOF

(71) Applicant: INSTITUTE OF MEDICAL BIOLOGY, CAMS, Kunming (CN)

(72) Inventors: Longding Liu, Kunming (CN); Li Yu, Kunming (CN); Guorun Jiang, Kunming (CN); Dandan Li, Kunming (CN); Heng Zhao, Kunming (CN); Huiwen Zheng, Kunming (CN); Ying Zhang, Kunming (CN); Yun Liao, Kunming (CN); Haijing Shi, Kunming (CN); Xin Zhao, Kunming (CN); Heng Li, Kunming (CN)

(73) Assignee: INSTITUTE OF MEDICAL BIOLOGY, CAMS, Kunming (CN)

( * ) Notice: Subject to any disclaimer, the term of this patent is extended or adjusted under 35 U.S.C. 154(b) by 0 days.

(21) Appl. No.: 18/654,901

(22) Filed: May 3, 2024

(30) Foreign Application Priority Data

Aug. 24, 2023 (CN) .......................... 202311074921.8
Nov. 9, 2023 (CN) ......................... 202311481600.X

(51) Int. Cl.
*C12N 7/00* (2006.01)
*C12N 5/071* (2010.01)

(52) U.S. Cl.
CPC .............. *C12N 7/00* (2013.01); *C12N 5/0688* (2013.01); *C12N 2500/02* (2013.01); *C12N 2523/00* (2013.01); *C12N 2770/32321* (2013.01); *C12N 2770/32351* (2013.01)

(58) Field of Classification Search
CPC .... C12N 7/00; C12N 5/0688; C12N 2523/00; C12N 2770/32321; C12N 2770/32351
See application file for complete search history.

(56) References Cited

FOREIGN PATENT DOCUMENTS

CN          114807060 A        7/2022

OTHER PUBLICATIONS

Feng et al., "A novel recombinant lineage's contribution to the outbreak of coxsackievirus A6-associated hand, foot and mouth disease in Shanghai, China, 2012-2013," Scientific Reports, 5:11700, Jun. 30, 2015.
He et al., "An emerging and expanding clade accounts for the persistent outbreak of Coxsackievirus A6-associated hand, foot, and mouth disease in China since 2013," Virology, 518:328-334, 2018.
Hu et al., "Six amino acids of VP1 switch along with pandemic of CV-A6-associated HFMD in Guangxi, southern China, 2010-2017," J. of Infection, 78:323-337, 2019.
Qiao et al., "Identification of recombinant coxsackievirus A6 variants in hand, foot and mouth disease in Nanjing, China, 2013," J. of Medi. Microbiol., 67:1120-1129, 2018.
Su et al., "Genome Sequence of a Human Coxsackievirus A6 Strain Isolated from a Severe Hand, Foot, and Mouth Disease Case in Qingdao, China, in 2017," Amer. Soc. for Microbiol., 9(17):e01449-19, 2020.
Tan et al., "Molecular epidemiology of coxsackievirus A6 associated with outbreaks of hand, foot, and mouth disease in Tianjin, China, in 2013," Arch Virol., 160(4): 1097-1104, 2015.
Xu et al., "Pathogenic characteristics of hand, foot and mouth disease in Shaanxi Province, China, 2010-2016," Scientific Reports, 10:989, 2020.
Zhang et al., "Continued Prevalence of Coxsackievirus A6 in Heilongjiang Province, China, from 2015 to 2018," Chinese Journal of Virology, 36(2):201-206, 2020.

*Primary Examiner* — Nicole Kinsey White
*Assistant Examiner* — Ruixue Wang
(74) *Attorney, Agent, or Firm* — Gavrilovich, Dodd & Lindsey LLP

(57) ABSTRACT

Provided is a Coxsackievirus A6 (CVA6) strain CVA6-KM-J33 and use thereof, and belongs to the technical field of biomedicine. The present invention provides a CVA6 strain CVA6-KM-J33, which belongs to a CVA6 virus. In the present invention, the strain CVA6-KM-J33 is susceptible to KMB17 cells and can achieve a relatively high titer. The strain has strong virulence, high pathogenicity and lethality to suckling mice, and desirable immunogenicity, and is a highly effective virus strain for CVA6 vaccine development. This strain can be used for immunogenicity evaluation or protective evaluation of CVA6 vaccine to improve the accuracy and reproducibility of vaccine immunogenicity evaluation. This strain can also be used to prepare animal models of Coxsackievirus (CV) infection, and exhibits desirable application prospects.

1 Claim, 8 Drawing Sheets

Specification includes a Sequence Listing.

| Positive strain | RT-PCR VP1 assay | | Neutralization test identification | | Result |
|---|---|---|---|---|---|
| | CA6 VP1 assay | CA10 VP1 assay | CA6 Standard serum | CA10 Standard serum | |
| KM-J33 | + | - | + | - | CA6 |

SEQUENCE LISTING

```
Sequence total quantity: 11
SEQ ID NO: 1              moltype = DNA  length = 21
FEATURE                   Location/Qualifiers
source                    1..21
                          mol_type = other DNA
                          note = Sequence of forward primer CVA6-1-F for RT-PCR
                            amplification
                          organism = synthetic construct
SEQUENCE: 1
tatagctctt ggagcagcac a                                                21

SEQ ID NO: 2              moltype = DNA  length = 25
FEATURE                   Location/Qualifiers
source                    1..25
                          mol_type = other DNA
                          note = Sequence of reverse primer CVA6-1-R for RT-PCR
                            amplification
                          organism = synthetic construct
SEQUENCE: 2
ttaccactct aaagttaccc acata                                            25

SEQ ID NO: 3              moltype = DNA  length = 18
FEATURE                   Location/Qualifiers
source                    1..18
                          mol_type = other DNA
                          note = Sequence of forward primer CA16-VP1-F for RT-PCR
                            amplification
                          organism = synthetic construct
SEQUENCE: 3
gcaaacggct aacataca                                                    18

SEQ ID NO: 4              moltype = DNA  length = 18
FEATURE                   Location/Qualifiers
source                    1..18
                          mol_type = other DNA
                          note = Sequence of reverse primer CA16-VP1-R for RT-PCR
                            amplification
                          organism = synthetic construct
SEQUENCE: 4
tgtccaaact ttcccaac                                                    18

SEQ ID NO: 5              moltype = DNA  length = 20
FEATURE                   Location/Qualifiers
source                    1..20
                          mol_type = other DNA
                          note = Sequence of forward primer EV71-VP1-F for RT-PCR
                            amplification
                          organism = synthetic construct
SEQUENCE: 5
aaggatgcta gtgatatcct                                                  20

SEQ ID NO: 6              moltype = DNA  length = 18
FEATURE                   Location/Qualifiers
source                    1..18
                          mol_type = other DNA
                          note = Sequence of reverse primer EV71-VP1-R for RT-PCR
                            amplification
                          organism = synthetic construct
SEQUENCE: 6
cattgtgagt ggcaagat                                                    18

SEQ ID NO: 7              moltype = DNA  length = 23
FEATURE                   Location/Qualifiers
source                    1..23
                          mol_type = other DNA
```

-continued

```
                         note = Sequence of forward primer CVA6-qP-F for RT qPCR
                          amplification
                         organism = synthetic construct
SEQUENCE: 7
taccaccggg araaacgtcc acg                                          23

SEQ ID NO: 8             moltype = DNA  length = 20
FEATURE                  Location/Qualifiers
source                   1..20
                         mol_type = other DNA
                         note = Sequence of reverse primer CVA6-qP-F for RT qPCR
                          amplification
                         organism = synthetic construct
SEQUENCE: 8
cggtcagytg cagtgttagt                                              20

SEQ ID NO: 9             moltype = DNA  length = 30
FEATURE                  Location/Qualifiers
source                   1..30
                         mol_type = other DNA
                         note = Sequence of probe for RT qPCR amplification
                         organism = synthetic construct
SEQUENCE: 9
acgtgagagc ttgggtacmt agaccccttc                                   30

SEQ ID NO: 10            moltype = AA  length = 160
FEATURE                  Location/Qualifiers
source                   1..160
                         mol_type = protein
                         note = Amino acid sequence of the VP1 structural protein of
                          the CVA6 strain CVA6-KM-J33
                         organism = enterovirus sp.
SEQUENCE: 10
TGASSNASDN TRCVMNRNGV NASVHYSRAG VGVVVKDSGT SDGYTVWDVM GVRRKSTYMR  60
DATVSNNNST TGMYMYVGAK DSRKSYWTAT NSAKSDVSVM SATAYWYDGY TGHKATNYGC  120
NNMMGHARTV SSTTGKNVHV RVYMRKHVRA WVRRSAYMVK                        160

SEQ ID NO: 11            moltype = RNA  length = 7435
FEATURE                  Location/Qualifiers
source                   1..7435
                         mol_type = genomic RNA
                         note = Nucleotide sequence of genomic RNA of the CVA6
                          strain CVA6-KM-J33
                         organism = enterovirus sp.
SEQUENCE: 11
ttaaaacagc ctgtgggttg cacccaccca cagggcccat tgggcgccag cacactgatt  60
ctacggaatc tttgtgcgcc tgttttataa ccccttcccc caaaactgta acttagaaga  120
atattacact actgatcaat agcaggcatg gcgcgccagt catgtctaga tcaagcactt  180
ctgtctcccc ggactgagta tcaatagact gctagcgcgg ttgaaggaga aaacgtccgt  240
tacccggcta actacttcga gaaacttagt agcaccattg aagctgcgga gtgtttcgtt  300
cagcactccc ccagtgtaga tcaggtcgat gagtcactgc actccccacg ggcgaccgtg  360
gcagtggctg cgttggcggc ctgcctatgg ggcaacccat aggacgctct aaagtggaca  420
tggtgcgaag agtctattga gctagttagt agtcctccgg cccctgaatg cggctaatcc  480
caactgcgga gcacatgccc ccaatccaga gggtggtgtg tcgtaacggg caactctgca  540
gcggaaccga ctactttggg tgtccgtgtt tccttttatt cttatattgg ctgcttatgg  600
tgacaattga gagattgtta ccatatagct attggattgg ccatccagtg acaaacagag  660
ctttgatata cttgtttgtg ggttttgttc cactcaccag tcgtacagtt cacaccctaa  720
agtacattct gattctaaac aatagaaaat gggcgcccaa gtttcaacag aaaaatctgg  780
gtcgcacgag acaaagaatg tagcgaccga agggtctact atcaatttca ccaacatcaa  840
ttactataag gattcttatg cagcgtcagc tagtagacag gactttgcgc aagaccccgc  900
aaagttcaca cgccccgtct tggataccat cagggaggtt gcagccccgc tgcaatcccc  960
ttctgttgag gcgtgcggtt atagtgaccg agttgcacag ttgactgtgg gcaactcgac  1020
cattaccacc caagaggcag ccaacattgt attgagttat ggagagtggc cagaatattg  1080
cccctccacg gatgctacag ctgtggacaa acctactcgc cctgacgtgt cagtgaatag  1140
gttctacaca ctgtcaacta agagttggaa gacagaatct actggttggt actggaaatt  1200
ccctgatgtg ctaaatgaca caggagtatt tggccaaaac gcccaattcc actacttgta  1260
ccgctcgggt ttctgcatgc acgttcagtg taatgcaagc aagttccatc agggagccct  1320
tttagtggct gcaatccccg aatttgtggt tgctgcaagc agccctgcca tgaaacctaa  1380
tggacaaggg ttgtacccag attttgccca cactaaccca ggtaaaaatg gccaagaatt  1440
tcgagatcct tatgtcttgg atgctggtgt cccccctaagt caagcactgg tttacccccca  1500
tcaatggatc aatctacgaa ctaataactg cgcgaccatt attatgccat acgtcaatgc  1560
gctcccattt gattcagcac ttaaccactc gaattttgga ttggttgtga tccctattag  1620
ccccttaaaa tattgtaatg gggccactac agaagtgcca atcacactaa ctattgctcc  1680
acttaactcg gagtttagcg gtctccgaca agcaataaaa caagggttcc ccacagagct  1740
caagcctggt accaatcaat ttctcacaac tgatgatggg acgtccccac caatactgcc  1800
tggttttgaa ccaactccat tgattcacat tcctggtgag ttcacctcct tgttagattt  1860
atgtcaaata gaaaccatac tagaagtcaa taacaccact ggcaccactg gagtcagtag  1920
attactaatc cccgttcgag cacagaacaa tgtggaccaa ttgtgcgcat cattccaagt  1980
agaccctggg cgcaatggcc cgtggcaatc cacaatggtc ggccagatct gcaggtacta  2040
```

```
cactcaatgg tcaggttccc ttaaggtaac ctttatgttc acaggttctt ttatggctac   2100
agggaaaatg ctgatagcct atacaccacc tggtagtgct cagcccgcta caagggaagc   2160
agcaatgctt gggactcata tagtgtggga ttttggtttg caatcatcgg ctaccctggt   2220
catacccttgg attagtaata cccattttag agcagttaag actggagggg tttacgacta   2280
ctacgcaacc gggattgtca ccatttggta ccaaaccacc tttgtggtgc caccagacac   2340
ccccactgag gctaatatta tagctctttgg agcagcacag aaaaatttta ccctaaagct   2400
gtgtaaggac actgacgaga tccagcaaac agcagagtac caaaatgatc ccattacaaa   2460
tgcagtggaa agcgctgtga gcgcgcttgc tgacaccaca atatcccggg tgaccgcagc   2520
caatactgta gctagcactc actccctggg aacagggcgt gtaccagcat tgcaagccgc   2580
agaaacggga gcaagctcta atgccagtga tgagaacctt attgagaccc gctgtgtgat   2640
gaatcgaaac ggggttaatg aggcgagtgt ggaacacttt tactctcgtg cagggctggt   2700
aggagttgtg gaggtgaagg actcgggtac tagcctggat gggtacacag tttggcccat   2760
agatgtgatg ggcttcgtgc aacagcggcg caagctagag ttgtcaacat acatgcgctt   2820
tgatgccgag ttcactttttg tgtccaacct caataacagc acgcacccccg ggatgctgct   2880
gcagtacatg tatgtgccac caggggcccc taagccagat agcaggaaat cataccaatg   2940
gcagaccgct actaacccgt caatattcgc aaaattgagt gatccacccc ccaggtatc    3000
tgtcccgttc atgtcgccag caacggctta tcagtggttt tatgacggat accctacatt   3060
tggtgaacac aaacaagcca ccaatttgca atatgggcaa tgtcctaata acatgatggg   3120
ccatttttgct atccgaacag tcagtgaatc taccactggg aaaaacgtcc acgttcgggt   3180
gtacatgaga attaagcacg tgagagcttg ggtacctaga ccccttcgat cccaagcata   3240
tatggtcaag aactacccga catacagcca acaataact aacactgcgg ctgaccgtgc    3300
aagcataacc accacggatt atgaaggcgg ggtaccagca aaccacaga ggacatctga     3360
taggttaggt caacaatccg gggctatcta tgtaggcaac ttcagagtgg taaaccgaca   3420
tctcgccact cgtaatgatt gggcaaatct agtatgggaa agtagctcac gagatctctt   3480
ggtgtcctcc accactgctc agggatgtga caccattgcc cgatgtgatt gtcaaacagg   3540
agtgtattac tgcaactcta aaaggaaaca ctacccgtta agttttttcta agcccagcct   3600
cgtctttgtg gaagctagtg agtattaccc tgccaggtat cagtcacacc ttatgcttgc   3660
gaagggacat tctgaacccg gggactgtgg cggcattctt aggtgccaac atggcgtgat   3720
tggcatcgtg tccactggtg gtaatggact tgttggattt gcagatatca gagaccttct   3780
gtggctggat gaagaagcta tggaacaggg tgtgtcagat tacatcaaag ggctcggtga   3840
cgcatttgga actggcttta ctgatgcagt agctaggcaa gtggaggctc ttaagaacta   3900
cctaatagga tctgaagggg ctgttgaaaa gatcttaaag aatttaatta agctgatctc   3960
agcattagtc atagtgatca gaagtgatta tgacatggta accctcacag caaccttggc   4020
actcataggg tgtcatggca gcccttgggc gtggataaga gctaagacag catccatcct   4080
aggcattcct atcgcccaga agcagagtgc atcatggctc aagaagttta atgacatggc   4140
caatgctgcc aagggttttg agtggattc caataaaatc agcaaatttta ttgattggct   4200
taaggagaaa attataccag cggccagaga aaggttgaa ttttttgaaca acctaaaaca    4260
actgccattg ttggagaacc aaatttcaaa cctggagcag tccgccgctt cgcaggaaga   4320
ccttgaggca atgtttggga acgtatcgta cctcgctcac ttctgccgta aataccaacc   4380
actttatgct acagaagcca aaagagttta tgccttggaa aagaggatga acaattacat   4440
gcagttcaag agcaaacacc gtattgaacc tgtatgtctt atcatcagag ctccccagg    4500
cactggaaag tccttagcaa ccggtataat tgcccgagca atagctgaca aataccactc   4560
tagtgtgtac tcactcccgc cagatccaga ccacttgtt ggatacaaac agcaagtggt     4620
cacagtttatg gacgatctat gccaaaatcc tgatgcaag gatatgtcac tctttttgtca    4680
gatggtatcc actgctagatt ttatcccacc aatggcttct ttgaagagaa aaggggtttc   4740
attcacatct aaatttgtta ttgcatccac taatgccagc aacatcatag tgccaacggt   4800
gtctgactct gatgctattc gccgcaggtt ctatatgac tgcgacatcg aggtaacgga     4860
ctcgtataaa acagatttgg gtaggttgga tgctggaaga gctgccaaat tgtgctctga   4920
aaataacaca gcaaacttca aacgctctag cccactagtg tgtgggaagg ccatccaatt   4980
aagagatagg aagtctaagg ttagatacag tgtggatacg tgtttcag agctcataag    5040
ggaatacaat aacaggtctg ccattggaaa caccaattgaa gcgttgttcc agggggccaa   5100
caagtttaga cccattagaa ttagtcttga ggaggcgcca gcaccagatg ttattagtga   5160
tctacttgcc agtgtggata gtgaagaggg gcgccaatac tgtagagacc agggttggat   5220
tataccagaa acccctacca acgttgagcg acatttaagt agggccgtgc taatcatgca   5280
atccattgcc acggtcgttg cagtggtctc actggtgtat gttatctaca gcttttttgc   5340
tggatttcag ggtgcgtact ctggcgctcc taagcaagtg ctcaagaaac ccatcctccg   5400
cacggcaaca gtgcaaggac ctagccttga cttttgccta tccctactga gaaggaacat   5460
caggcaggtt cagacagatc aagggcactt cactatgctg ggtgtcaggg atcgcttagc   5520
agttctcccg cgccactcgc agcccggaaa agcaatctgg gtggaacaca aactcgtgaa   5580
catcctggat gctgtcgagt tggtgatga gcaaggggtt aacctagagc tcactctaat    5640
cactcttgat accaatgaga aattcagaga tatcaccaag ttcattccag aaaacatcag   5700
tgctgctagt gacgccaccc tagtgattaa tacagaacac atgccctcaa tgtttgtacc   5760
tgtgggagat gtcgtgcaat acggtttcct gaatctcagt ggaaagccca cccatcgcac   5820
tatgatgtac aacttcccta ctaaggcagg acagtgttgga catcagttgga   5880
gaaagttatt ggaattcaca taggaggcaa tggtaggcaa ggtttctgtg cgggacttaa   5940
gaggagctac tttgccagtg agcaaggaga atccaatgg gtaaagccta caaagaaac      6000
tgggagactc aacatcaacg ggccaactcg cactaagctc gaacctagtg tgttccatga   6060
tatctttgag ggcaacaagg aaccagcggt cttacacagc aaagaccctc gtctcgaggt   6120
ggattttgaa caggcattgt tctccaagta tgtaggaaac actatacatg agcctgatga   6180
atatatcaag gaggcagcct tacattatgc aaatcagttg aagcagctaa atatagacac   6240
ttctcaaatg agcatggaag aggcttgcta cttcccagac aaccttgaag ctattgaacct    6300
tcacactagt gcaggctacc cctacagtgc cttgggatc aagaagaggg atatcttaga    6360
ccccaccacc agggatgtga gtaagatgaa gttctacatg gacaagtatg gtcttgatct   6420
ccctttactct acttatgtta aggatgagct acgctcaata gataagatca agaagggaaac   6480
atcccgctta attgaagcta gcagtttgaa cgactcagtt tacctcagaa tggcttcgg    6540
acatctctat gaaactttcc atgcaaaccc tgggactgtg actggttcgg ctgtgggttg   6600
taaccccgga ctgttctgga gcaagttgcc aatcctgctc cctggttccc tctttgcttt   6660
tgactactcg ggctatgatg ctagtctcag cccagttttgg ttcagagcat tggagctagt   6720
tcttagagag ataggttaca gtgacgaggc aatctcgctc attgaaggga tcaatcatac   6780
```

-continued

```
acaccatgta taccgcaaca aaacttattg cgtacttggt gggatgccat caggctgttc  6840
aggaacatcc attttcaact caatgattaa caacatcatc attagatcat tgcttatcaa  6900
aacatttaag ggtattgacc tagatgaact caacatggtt gcttatgggg acgatgtact  6960
tgctagttac ccttttccta ttgactgctc agaactagca agaacaggca aggagtatgg  7020
tttaaccatg acccccgcgg ataagtctcc ttgcttcaat gaagttaatt gggaaaatgc  7080
aacctttctt aagaggggtt tcttgcctga tgaacaattt ccatttttga ttcaccccac  7140
catgccaatg aaggagatcc acgaatccat tcggtggacc aaggatgcac gcaatactca  7200
agatcacgtg cgatccttgt gtctattggc gtggcacaac ggcaaacaag aatatgaaaa  7260
atttgtaagt gcaattaggt ctgtcccaat aggaaaggca ctggctattc caaattatga  7320
aaacctgaga cgcaattggc tcgaattatt ttagaggtcg aatacacctc aaccccacca  7380
ggaatctggt cgtgaatatg actggtgggg gtaaatttgt tataaccaga atagc       7435
```

COXSACKIEVIRUS A6 STRAIN CVA6-KM-J33 AND USE THEREOF

CROSS-REFERENCE TO RELATED APPLICATION

This patent application claims the benefit and priority of the Chinese Patent Application No. 202311074921.8 filed with the China National Intellectual Property Administration on Aug. 24, 2023, and the Chinese Patent Application No. 202311481600.X filed with the China National Intellectual Property Administration on Nov. 9, 2023, the contents of which are incorporated by reference herein in its entirety as part of the present application.

REFERENCE TO SEQUENCE LISTING

A computer readable XML file entitled "GWP20240200991_sequence listing.xml", which was created on Mar. 26, 2024 with a file size of about 20,625 bytes, contains the sequence listing for this application, has been filed with this application, and is hereby incorporated by reference in its entirety.

Microorganism Deposit

Exemplary microorganism of the disclosure Coxsackievirus CVA6-KM-J33 was deposited on Aug. 6, 2023 with the China Center for Type Culture Collection (CCTCC), as accession number CCTCC NO. V202384 under the Budapest Treaty. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions imposed by the depositor on the availability to the public of the deposited material will be irrevocably removed upon the granting of the patent.

TECHNICAL FIELD

The present disclosure belongs to the technical field of biomedicine, and specifically relates to a Coxsackie virus A6 (CVA6) strain CVA6-KM-J33 and use thereof.

BACKGROUND

Hand-foot-mouth disease (HFMD) in children is a viral infectious disease that has been emerging in children in different regions around the world, especially in the Asia-Pacific region over the past 20 years. Since 2000, the incidence rate of HFMD has been concentrated in East Asia, and the cases of severe HFMD mainly manifesting neurological clinical symptoms account for about 1.5% to 2%. Some of the sick children have developed neurogenic pulmonary edema and even died due to damage to the cardiovascular system in a short period of time caused by damage to the nervous system. The HFMD thus poses a serious public health problem.

Research on the etiology of HFMD shows that this disease can be caused by a variety of human enteroviruses. Among them, in addition to enterovirus EV71, the main pathogens are Coxsackievirus A16 (CVA16) and Coxsackievirus A6 (CVA6). Sample surveys in most areas of China since 2013 have shown that the proportion of cases caused by CVA6 in the total incidence of children is about not less than 35% to 39% of the total number of cases [1-9]. Due to the application of EV71 and CVA6 vaccines, the proportion of patients caused by CVA6 has gradually increased in various regions. At the same time, clinical and epidemiological analysis of CVA6 infection cases also suggests that the proportion of severe cases has also increased among CVA6 infection patients. Therefore, it is extremely necessary to screen out a CVA6 strain with desirable neutralizing ability, genetic stability, and strong virulence.

CVA6 virus is an enterovirus and has similar structural characteristics to those of the EV71 and CVA16. As members of the genus Picornavirus, antigenic composition patterns of the above three viruses are also highly similar. All three viruses encode four structural proteins VP1, VP2, VP3, and VP4. Moreover, a capsid composed of three of these proteins works on the immune system to induce a complete immune response. Enteroviruses that cause HFMD mainly include four types: EV-A, EV-B, EV-C, and EV-D. The Coxsackievirus A6 (CVA6) strain belongs to an enterovirus group A that has a total of 16 subtypes, including 11 subtypes A and 5 subtypes B. According to different genotypes, the CVA6 is divided into five branches A to E. Currently, all CVA6 epidemic strains worldwide belong to type D, which are divided into subtypes D1, D2, and D3. The D3 subtype can be further subdivided into types D3a and D3b.

At present, the pathogenesis of HFMD is still unclear, and particularly the pathogenic mechanism of CVA6 has not been reported, making the screening of anti-CVA6 drugs and vaccines of great significance. In addition, since mice are generally less susceptible to clinically isolated strains, only a few clinically isolated viruses can infect mice. Accordingly, it is also of great significance to screen strains that can be used to construct animal models of CVA6 infection.

CITED REFERENCES

[1] Su Z, Shi X, Zhang F, Chai Q, Gong J, Wang Z. Genome Sequence of a Human Coxsackievirus A6 Strain Isolated from a Severe Hand, Foot, and Mouth Disease Case in Qingdao, China, in 2017. *Microbiol Resour Announc.* 2020 Apr. 23; 9 (17): c01449-19. DOI: 10.1128/MRA.01449-19. PMID: 32327512; PMCID: PMC7180285.

[2] ZHANG Man, CHEN Shuhong, ZHANG Yong, et al. Continued Prevalence of CVA6 in Heilongjiang Province, China, from 2015 to 2018 [J]. *Acta Virologica Sinica,* 2020, 36 (02): 201-206. DOI: 10.13242/j.cnki.bingduxuebao.003665.

[3] Tan X, Li L, Zhang B, Jorba J, Su X, Ji T, Yang D, Lv L, Li J, Xu W. Molecular epidemiology of Coxsackievirus A6 associated with outbreaks of hand, foot, and mouth disease in Tianjin, China, in 2013. *Arch Virol.* 2015 April; 160 (4): 1097-10$^4$. DOI: 10.1007/s00705-015-2340-3. Epub 2015 Feb. 15. PMID: 25680566; PMCID: PMC4629805.

[4] Qiao M, Yong W, Wang X, Li W, Zhang Z, He M, Shi L, Wang Y, Xie G, Ding J. Identification of recombinant Coxsackievirus A6 variants in hand, foot and mouth disease in Nanjing, China, 2013. *J Med Microbiol.* 2018 August; 67 (8): 1120-1129. DOI: 10.1099/jmm.0.000780. Epub 2018 Jun. 27. PMID: 29947601.

[5] He S, Chen M, Wu W, Yan Q, Zhuo Z, Su X, Zhang S, Ge S, Xia N. An emerging and expanding clade accounts for the persistent outbreak of Coxsackievirus A6-associated hand, foot, and mouth disease in China since 2013. *Virology.* 2018 May; 518:328-334. DOI: 10.1016/j.virol.2018.03.012. Epub 2018 Mar. 26. PMID: 29587191.

[6] Chen M, Zuo X, Tan Y, Ju Y, Bi F, Wang H, Chen M. Six amino acids of VP1 switch along with pandemic of CV-A6-associated HFMD in Guangxi, southern China, 2010-2017. *J Infect.* 2019 April; 78 (4): 323-337. DOI: 10.1016/j.jinf.2019.02.002. Epub 2019 Feb. 14. PMID: 30771363.

[7] Xu Y, Zheng Y, Shi W, Guan L, Yu P, Xu J, Zhang L, Ma P, Xu J. Pathogenic characteristics of hand, foot and mouth disease in Shaanxi Province, China, 2010-2016. *Sci Rep.* 2020 Jan. 22; 10 (1): 989. DOI: 10.1038/s41598-020-57807-z. PMID: 31969644; PMCID: PMC6976675.

[8] Xu Y, Zheng Y, Shi W, Guan L, Yu P, Xu J, Zhang L, Ma P, Xu J. Pathogenic characteristics of hand, foot and mouth disease in Shaanxi Province, China, 2010-2016. *Sci Rep.* 2020 Jan. 22; 10 (1): 989. DOI: 10.1038/s41598-020-57807-z. PMID: 31969644; PMCID: PMC6976675.

[9] Feng X, Guan W, Guo Y, Yu H, Zhang X, Cheng R, Wang Z, Zhang Z, Zhang J, Li H, Zhuang Y, Zhang H, Lu Z, Li M, Yu H, Bao Y, Hu Y, Yao Z. A novel recombinant lineage's contribution to the outbreak of coxsackievirusA6-associated hand, foot and mouth disease in Shanghai, China, 2012-2013. *Sci Rep.* 2015 Jun. 30; 5:11700. DOI: 10.1038/srep11700. PMID: 26121916; PMCID: PMC4485158.

SUMMARY

An objective of the present disclosure is to provide a CVA6 strain CVA6-KM-J33 and use thereof. The CVA6 strain CVA6-KM-J33 has desirable cross-neutralizing ability, genetic stability, and strong virulence.

The present disclosure provides a CVA6 strain CVA6-KM-J33 with a deposit number of CCTCC NO. V202384 in the China Center for Type Culture Collection (CCTCC).

Preferably, a VP1 structural protein of the CVA6 strain CVA6-KM-J33 has the amino acid sequence set forth in SEQ ID NO:10.

The present disclosure further provides a propagation and passage method for the CVA6 strain CVA6-KM-J33, including conducting propagation and passage using a human diploid cell as a stromal cell.

Preferably, the human diploid cell includes a human embryonic lung diploid cell KMB17.

Preferably, the human embryonic lung diploid cell KMB17 is infected with the CVA6 strain CVA6-KM-J33 and then cultured at 37° C. under 5%$^+$ $CO_2$.

The present disclosure further provides a biological agent prepared using a genomic RNA of the CVA6 strain CVA6-KM-J33.

Preferably, the genomic RNA has the nucleotide sequence set forth in SEQ ID NO: 11.

The present disclosure further provides an antiserum against a CVA6 strain, where a preparation process of the antiserum includes injecting the CVA6 strain CVA6-KM-J33 into an animal and collecting serum of the animal to obtain the antiserum.

The present disclosure further provides a vaccine or a medicament for preventing and/or treating a CVA6 strain-caused disease, where an active ingredient of the vaccine or the drug includes the biological agent or the antiserum.

The present disclosure further provides the use of an inactivated strain of the CVA6 strain CVA6-KM-J33 as a drug delivery medium.

Beneficial effects: the present disclosure provides a CVA6 strain CVA6-KM-J33, which belongs to CVA6 virus. In the present disclosure, the strain CVA6-KM-J33 is isolated from Vero cells, amplified for 3 generations, and then inoculated on KMB17 cells for adaptive passage. The strain is susceptible to KMB17 cells and can achieve a relatively high titer. The strain has strong virulence, high pathogenicity and lethality to suckling mice, and desirable immunogenicity, and is a highly effective virus strain. This strain can be used for immunogenicity evaluation or protective evaluation of CVA6 vaccine to improve the accuracy and reproducibility of vaccine immunogenicity evaluation. This strain can also be used to prepare animal models of Coxsackievirus (CV) infection and exhibits desirable application prospects.

Deposit of Biological Material

The CVA6 strain CVA6-KM-J33 was deposited at the CCTCC on Aug. 6, 2023, in Wuhan University, Wuhan, China, with a deposit number of CCTCC NO. V202384.

BRIEF DESCRIPTION OF THE DRAWINGS

FIG. 6A is the change of viral load in each tissue with the number of days of infection after intracerebral injection of $10^5$ $CCID_{50}$/mouse infected with CV-A6 virus in 1-day-old suckling mice; FIG. 6B is the change of viral load in each tissue with the number of days of infection after intracerebral injection of $10^6$ $CCID_{50}$/mouse infected with CV-A6 virus in 1-day-old suckling mice; FIG. 6C is the change of viral load in each tissue with the number of days of infection after intracerebral injection of $10^7$ $CCID_{50}$/mouse infected with CV-A6 virus in 1-day-old suckling mice; the base of log is 10;

FIG. 7A is normal lung tissues; FIG. 7B is lung-endothelial cell necrosis and shedding; FIG. 7C is normal brain tissues; FIG. 7D is brain-local (cerebellum) focal hemorrhage, with fewer brain neuron cells, mild edema, and pyknosis of individual cell nuclei;

FIG. 8A is the neutralizing antibody seroconversion rate of serum before and after booster immunization at different doses; FIG. 8B is the comparison of neutralizing antibody titers in mice immunized by three routes; 35 days: the 7th day after the booster immunization.

DETAILED DESCRIPTION OF THE EMBODIMENTS

Figure 1:
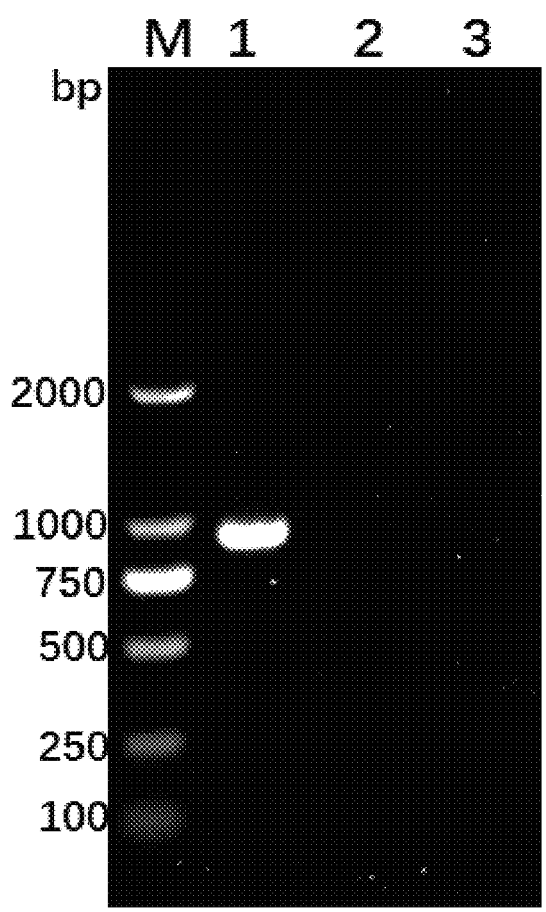
FIG. 1 shows an electrophoresis pattern of the RT-PCR amplification product in Example 1 of the present disclosure.

The present disclosure provides a CVA6 strain CVA6-KM-J33 with a deposit number of CCTCC NO. V202384 in the CCTCC.

In the present disclosure, the strain CVA6-KM-J33 is isolated from Vero cells, amplified for 3 generations and then inoculated on KMB17 cells for adaptive passage. This strain is susceptible to KMB17 cells and can achieve a relatively high titer. This strain has strong virulence, high pathogenicity and lethality to suckling mice, and desirable immunogenicity, and is a highly effective virus strain.

In the present disclosure, a VP1 structural protein of the CVA6 strain CVA6-KM-J33 has the amino acid sequence shown in SEQ ID NO: 10, indicating that this strain belongs to a CVA6 virus.

The present disclosure further provides a propagation and passage method of the CVA6 strain CVA6-KM-J33, including conducting propagation and passage using a human diploid cell as a stromal cell.

In the present disclosure, the human diploid cell preferably includes a human embryonic lung diploid cell KMB17. The human embryonic lung diploid cell KMB17 is a human-derived cell line independently developed and established by the Institute of Medical Biology, Chinese Academy of Medical Sciences. Preferably, the human embryonic lung diploid cell KMB17 is infected with the CVA6 strain CVA6-KM-J33 and then cultured at 37° C. under 5% $CO_2$. Under the culture conditions, cytopathic effect is observed in not less than 75% of the cells within 72 h to 96 h.

The present disclosure further provides a biological agent prepared using a genomic RNA of the CVA6 strain CVA6-KM-J33.

In the present disclosure, the biological agent preferably includes any one of the following items:
1) a nucleic acid molecule encoding the genomic RNA of the CVA6 strain;
2) an expression cassette carrying the nucleic acid molecule in 1);
3) a recombinant vector carrying the nucleic acid molecule in 1) or a recombinant vector carrying the expression cassette in 2);
4) a recombinant microorganism carrying the nucleic acid molecule in 1), a recombinant microorganism carrying the expression cassette in 2), or a recombinant microorganism carrying the recombinant vector in 3);
5) a cell line carrying the nucleic acid molecule in 1) or a cell line carrying the expression cassette in 2); and
6) an animal model constructed using the strain.

In the present disclosure, the animal model is preferably based on mice, such as Balb/c mice to establish the animal model. The genomic RNA has the nucleotide sequence preferably set forth in SEQ ID NO: 11.

The present disclosure further provides an antiserum against a CVA6 strain, where a preparation process of the antiserum includes injecting the CVA6 strain CVA6-KM-J33 into an animal and collecting a serum of the animal to obtain the antiserum.

In the present disclosure, there is no special limitation on the type of the animal, and animals for conventional antiserum preparation in this field can be used.

The present disclosure further provides a vaccine or a drug for preventing and/or treating a CVA6 strain-caused disease, where an active ingredient of the vaccine or the drug includes the biological agent or the antiserum.

In the present disclosure, the CVA6 strain can produce immune effects through multiple immune routes, such as intradermal, intramuscular, and intradermal routes. After immunizing mice, the antibody titer can reach up to 1:1024, showing desirable immunogenicity, and can be used to prepare virus-free vaccines.

The present disclosure further provides the use of an inactivated strain of the CVA6 strain CVA6-KM-J33 as a drug delivery medium.

In the present disclosure, the CVA6 strain CVA6-KM-J33 has desirable infectivity and can be used as a drug delivery medium for drug delivery after inactivation.

To further illustrate the present disclosure, the CVA6 strain CVA6-KM-J33 and the use thereof provided by the present disclosure are described in detail below in combination with examples, but these examples should not be construed as limiting the claimed scope of the present disclosure.

Example 1 Isolation and Identification of CVA6 Strain CVA6-KM-J33

1. Processing of clinical samples: anal swab samples were collected from children diagnosed with HFMD by the Yunnan Provincial Center for Disease Control and Prevention into 15 mL sterile centrifuge tubes, and 1 mL of 0.01 M PBS was added. The anal swab clinical specimen was fully oscillated with an oscillator, centrifuged at 4,000 rpm for 20 min, a supernatant was collected and an equal volume of chloroform was added, mixed repeatedly, centrifuged at 2,800 rpm for 15 min, and a supernatant was collected.

2. Virus isolation and culture: viruses were cultured and isolated on Vero cells, cultured statically at 37° C., 5% $CO_2$, and observed continuously for 7 d. If cytopathic effect was observed in not less than 80% of the cells under the microscope, the virus fluid was collected. Passaging 3 times in this way could eliminate cell lesions caused by chloroform or other factors.

3. Virus harvesting and adaptive subculture in KMB17 cells: within 24 h to 48 h after KMB17 cell subculture, when the cell area approached 90%, the growth medium was discarded and the cells were washed once with PBS. After discarding the PBS, a serum-free maintenance solution was added to the cells, shaken gently, and then the maintenance solution was removed. An appropriate amount of the virus liquid was inoculated into the culture bottle, adsorbed at 37° C. for 1 h, an appropriate amount of the maintenance solution was added, and cultured at 37° C. When distinct cytopathic effect was observed in not less than 80% of the cells under a microscope, the culture bottle was frozen in a −30° C. refrigerator.

4. Virus identification: After 3 times of adaptive subculture, the virus liquid was obtained, and the harvested virus liquid was initially identified, including molecular biology identification (nucleic acid sequence determination and subtype analysis), research on cross-neutralization capabilities, and genome sequencing, so as to initially screen virus strains.

4.1. Molecular biology identification: RT-PCR was conducted to identify CVA6, CVA6-positive strains were subjected to VP1 nucleic acid sequence determination, and CVA6 genotyping was conducted based on the obtained VP1 nucleotide sequence.

1) The uploaded CV-A6 gene sequences in GenBank were selected as reference sequences (the reference sequences had gene accession numbers of MN845834.1 and MN845849.1, respectively), and the primers for the VP1 segment shown in Table 1 were designed using a Primer-BLAST primer design function in the National Center for Biotechnology Information (NCBI).

TABLE 1

Primer sequences for RT-PCR amplification

| Primer name | Primer sequence (5'-3') | Product size |
| --- | --- | --- |
| CVA6-1-F | SEQ ID NO: 1: TATAGCTCTTGGAGCAGCACA | 914 bp |
| CVA6-1-R | SEQ ID NO: 2: TTACCACTCTAAAGTTACCCACATA | |
| CA16-VP1-F | SEQ ID NO: 3: GCAAACGGCTAACATACA | 932 bp |
| CA16-VP1-R | SEQ ID NO: 4: TGTCCAAACTTTCCCAAC | |
| EV71-VP1-F | SEQ ID NO: 5: AAGGATGCTAGTGATATCCT | 1009 bp |
| EV71-VP1-R | SEQ ID NO: 6: CATTGTGAGTGGCAAGAT | |

2) Viral nucleic acid was extracted using the AxyPrep body fluid viral DNA/RNA mini kit, and the VP1 fragment was amplified using the PrimeScript™ One Step RT-PCR Kit produced by Takara Bio (Dalian) Co., Ltd. The reaction conditions included: 50° C. for 30 min; 94° C. for 2 min; 35 cycles of 94° C. for 30 s, 50° C. for 30 s, and 72° C. for 1 min; and 72° C. for 10 min.

3) The target fragment was identified by 1% agarose gel electrophoresis and sent to Shanghai Sangon Biotech Co., Ltd. for sequencing. Germline evolution analysis was performed using MEGA5.0 software.

Figure 2:
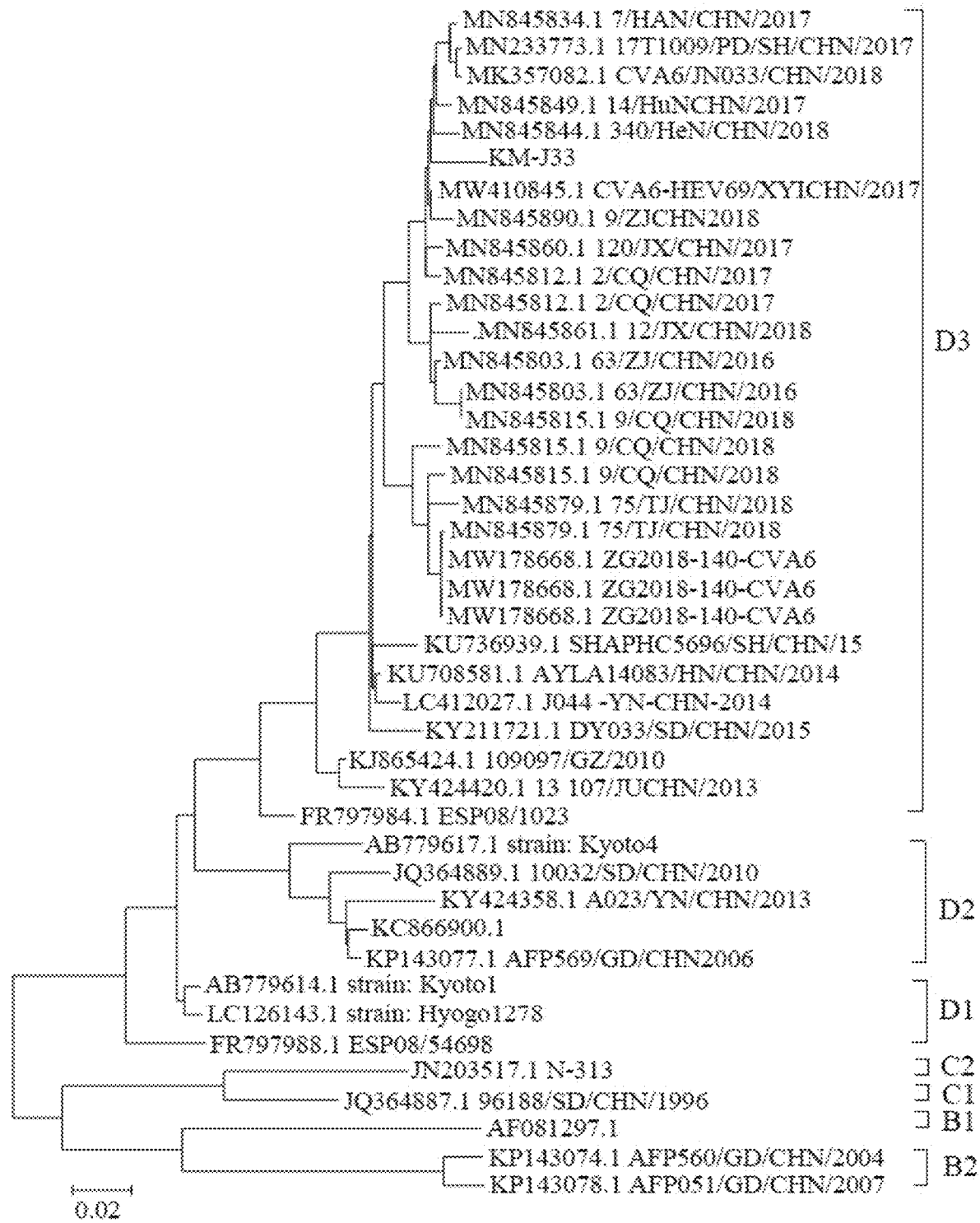
FIG. 2 shows a phylogenetic tree based on VP1 region nucleotides of the CVA6-KM-J33 in Example 1 of the present disclosure.

A target band with a size of 914 bp was observed in the positive sample using CVA6 VP1-specific primers, but no bands appeared in the amplification using EV71 and CA16 primers again, as shown in FIG. 1 (where Lane 1 was the amplification product of CVA6-1 primer, and Lanes 2 and 3 were the amplification products of EV71-VP1 and CA16-VP1 primers). Viruses identified as CVA6-positive were genotyped for CVA6 based on the VP1 nucleic acid sequence. The results showed a B3 type. The phylogenetic tree of the CVA6 based on the VP1 region nucleotide sequence is shown in FIG. 2.

Figures 3, 4:
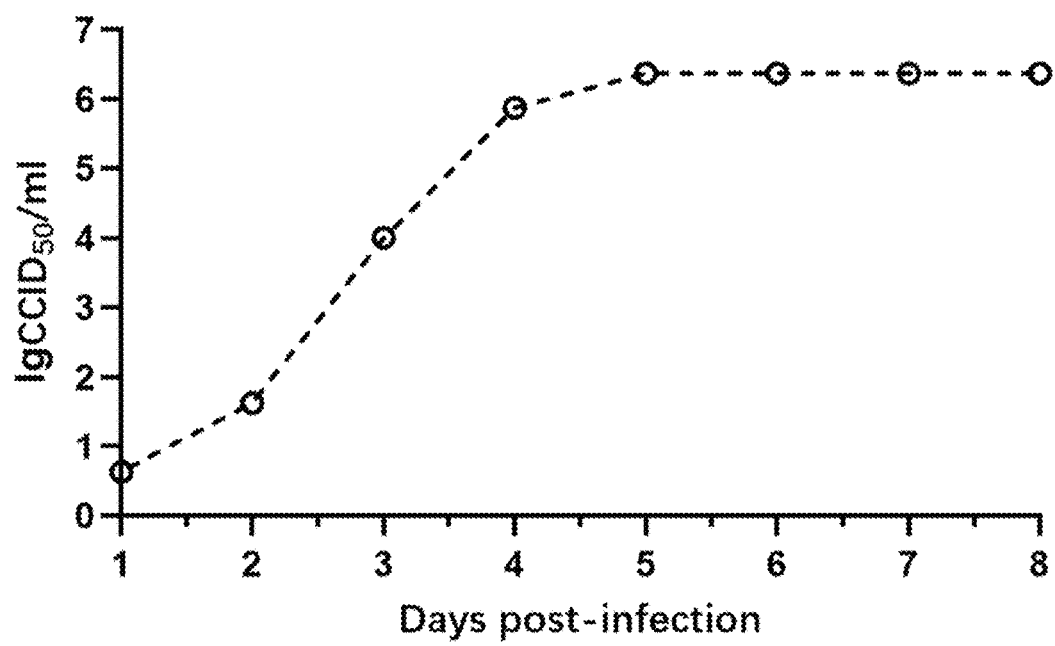
FIG. 3 shows the test results of a cross-neutralizing ability in Example 1 of the present disclosure.
FIG. 4 shows a growth curve of the virus strain in Example 4 of the present disclosure in human diploid cells KMB17.

4.3. Establishment of candidate strains for neutralizing antibody detection: validation of CVA6-KM-J33 was conducted. The results showed that this strain only had a specific neutralizing ability against the immune serum of CVA6, but had no cross-reactivity against the immune serum of other enteroviruses such as EVA71, CVA10, and CVA16, as shown in FIG. 3. The results proved that this strain was suitable for detecting the neutralizing antibody titer of immune serum of the CVA6 strain.

Example 2 Preparation of CVA6 Standard Serum

1. Crude Purification for Virus Liquid of CVA6 Reference Strain

Vero cells were inoculated in a culture bottle. When the cell area was inoculated close to 90%, an appropriate amount of CVA6 reference strain GS2015-399 (from the Institute of Viral Disease Prevention and Control, Chinese Center for Disease Control and Prevention) was inoculated and placed in a 37° C. 5% $CO_2$ incubator for adsorption for 1 h, added with an appropriate amount of serum-free maintenance solution, and cultured statically until cytopathic effect was observed in not less than 80%, and the virus liquid was harvested. The 15-399 virus harvest solution was centrifuged at 100,000×g for 4 h at 4° C., resuspended in 0.01 M PBS, extracted once with ½ volume of chloroform, centrifuged at 2,800 rpm for 20 min at room temperature, and a supernatant was collected to obtain crudely purified virus liquid.

2. Preparation of Standard Serum

During primary immunization, the 15-399 crude virus solution and a Freund's complete adjuvant were thoroughly mixed at a volume of 1:1, and injected subcutaneously at multiple points to immunize Japanese big-eared rabbits, 1 mL/rabbit. 28 d after the primary immunization, the crude virus liquid and an equal volume of Freund's incomplete adjuvant were fully mixed to allow booster immunization 4 times, while the control group was injected with an equal dose of PBS, and the growth of rabbit was continuously observed and recorded. Blood was collected from the car vein on the 28th day after the primary immunization and the 14th day after the booster immunization, and the neutralizing antibodies in the isolated serum had a titer of 1:2048 to 1:8192.

3. Negative Serum

The serum isolated from Japanese big-eared rabbits that had not been immunized with virus fluid and collected from the car vein was used as the negative serum used in the identification experiment.

Example 3 Preliminary Purification and Amplification of CVA6 Strain

1. A virus dilution of the initially screened virus strain in Example 1 was inoculated into a 6-well cell culture plate for purification.

1.1 Cell preparation: KMB17 cells were inoculated in a 6-well plate in advance and cultured. When the monolayer became dense, the original medium was discarded, the cell surface was washed, and residual bovine serum and dead cells were removed by washing.

1.2 Virus preparation: the virus liquid was diluted at appropriate times.

1.3 Virus adsorption: the virus was inoculated into a 6-well plate, 0.4 mL/well, while a cell control was set up, the two groups were placed in a 5% $CO_2$ incubator at 37° C. to allow adsorption for 1 h to 2 h, where the cell plate was gently shaken several times every 15 min to 20 min to allow the virus to contact the entire cell surface during the adsorption.

1.4 Covering and culture: the virus liquid was discarded after the adsorption was completed, and the virus maintenance solution was added into the virus control and cell control wells at 3 ml/well. A mixture of agarose and virus maintenance solution was added into the remaining wells along the wall at 3 mL/well, allowed to stand at room temperature for not less than 30 min to cool and solidify into a covering layer. The culture plate with agarose was placed upside down in a 5% $CO_2$ incubator and cultured at 37±1° C., and the plaque status (morphology, size, and number) and cytopathic effect in the virus control were observed every day.

1.5 Plaque picking: when obvious plaques were seen under the microscope, a marker pen was used to mark the bottom of the 6-well plate at the corresponding position of the plaque; in a class II biosafety cabinet in the clean room, a 200 µL pipette was used to draw 20 µL of the mixed liquid at the marked position with the pipette tip under the liquid surface, and a total of 10 plaques of suitable size was selected.

1.6 Plaque culture: a 200 µL pipette tip with a filter element was used to select 10 single plaques into a 1.5 mL EP tube containing 100 µL of virus maintenance solution, pipetted and mixed repeatedly, inoculated into a 96-well cell culture plate where the cells have grown to a monolayer, cultured at 37±1° C. in a 5% $CO_2$ incubator, and CPE was observed every day. When the CPE of the cells reached 75%, a supernatant was collected and stored in a −20° C. refrigerator, and 3 virus clones that could cause the fastest pathogenesis of KMB17 cells were selected. At this time, the virus passage was P2. In this way, plaque purification was done 3 times continuously.

2. Identification and analysis: the virus clones selected for the third time were amplified, and infectivity titer testing was conducted on the virus clones selected each time and the virus amplification fluid from the third spot pick.

2.1 Although each clone strain selected was from the same strain of virus, there were differences in infectivity titers between clone strains, and the difference range was within 1 $lgCCID_{50}$/mL. In addition, the infectivity titers between clones increased with the rounds of plaque purification, and the infectivity titers of clones after the third plaque purification could reach a maximum of 6.25 $lgCCID_{50}$/mL.

2.2 The nucleic acid electrophoresis bands of the 9 spot-picked samples were single and bright, with a size of about 914 bp, which was consistent with expectations (FIG. 1), and no base mutation was found after the nucleic acid sequence comparison of VP1 gene of 9 spot picking samples. Therefore, it was believed that the 9 samples after plaque purification were still CVA6, and the base sequence and amino acid level of the VP1 region maintained certain stability.

Example 4 Detection of Infectivity Titer and Analysis of Growth Characteristics for CVA6 Strain CVA6-KM-J33 on KMB17 Cells The growth curve of strain CVA6-KM-J33 was observed on KMB17 cells, the virus liquid was harvested at 11 time points (0 h, 12 h, 24 h, 36 h, 48 h, 72 h, 96 h, 5 d, 6 d, 7 d, 8 d), and the infectious titer was measured detection. Virus titration: the infectivity titer of CVA6 was detected using the microcytopathy method and the virus growth characteristics were observed, and the results were calculated using Karber's formula:

1) KMB17 cells were prepared into a cell suspension and then counted, adjusted to a cell concentration of $1.0 \times 10^5$ cells/mL, inoculated into a 96-well plate (100 µL/well), and cultured in a 37° C. 5% $CO_2$ incubator for 24 h;
2) the CVA6 virus liquid was serially diluted 10 times with maintenance solution, from $10^{-1}$ to $10^{-8}$;
3) the 10-fold serially diluted virus solution to be tested was added into a 96-well plate having cells spread, with 8 parallel wells for each dilution, 100 µL/well, and 100 µL maintenance solution was added into the cell control group;
4) the cells were cultured in a 37° C. 5% $CO_2$ incubator;
5) the growth characteristics of KMB17 cells were analyzed, the occurrence of CPE in each dilution of cells was observed daily and the number of lesion wells was recorded until no more cell lesions formed;
6) the virus infectivity titer ($lgCCID_{50}$/mL) was calculated according to the Karber's method, and the average was taken after 3 replicated tests.

Experimental results: as shown in FIG. 4, an abscissa of the growth curve was the culture time, and an ordinate was the infectivity titer corresponding to the sampling time point. The one-step growth curve on KMB17 cells showed that the titer of strain CVA6-KM-J33 could reach the duplication peak at 72 h, and its infection titer reached 6.5 $CCID_{50}$/mL on the fourth day.

Example 5 In Vivo Pathogenicity Detection of CVA6 Strain CVA6-KM-J33

1-day-old SPF grade Balb/c suckling mice, 6 mice/group, were injected with different doses of CVA6-KM-J33 virus liquid via the intracerebral route while suckling mice in the control group were injected with equal doses of PBS. After 18 days of continuous observation, the growth, onset, and death of the suckling mice were recorded to evaluate the severity of the disease caused by the strain CVA6-KM-J33 at different doses. 3 infected suckling mice were sacrificed on days 3, 5, and 9 after infection, and their organs and tissues were collected for viral load detection. Histopathological examination (H&E staining) was conducted on the brain, lung, and heart tissues of suckling mice.

1. In this example, 1-day-old suckling mice were injected into the brain via the intracerebral route. The dosage groups were $10^4$ $CCID_{50}$/mouse, $10^5$ $CCID_{50}$/mouse, and $10^6$ $CCID_{50}$/mouse, while the control group suckling mice were given equal doses of PBS, with 6 mice in each group. Suckling mice began to become ill 3 days to 6 days after injection, and the latest onset time was the 6th day after injection. Compared with the control group, mice in different dose groups experienced varying degrees of morbidity and death. The symptoms of disease are shown in Table 2.

TABLE 2

Clinical standard score sheet

| Clinical score | Clinical manifestations |
| --- | --- |
| 0 | Health |
| 1 | Tiredness or lack of energy |
| 2 | Weight loss or weakness in the hind limbs |
| 3 | Paralysis of single hind limb |
| 4 | Paralysis of double hind limbs |
| 5 | Impending death or death |

Figure 5A:
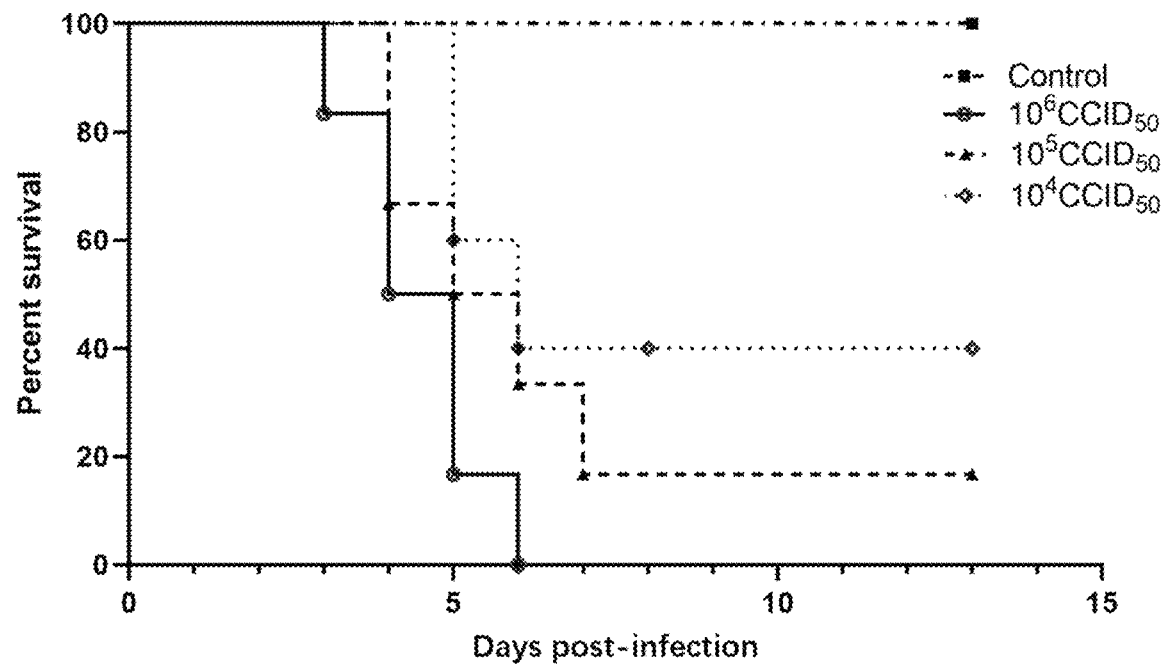
FIG. 5A-FIG. 5B show the clinical manifestations, survival rate (FIG. 5A), and evaluation of clinical symptom scores (FIG. 5B) of suckling mice inoculated with the strain CVA6-KM-J33 at different infection doses in Example 5 of the present disclosure.
Figure 5B:
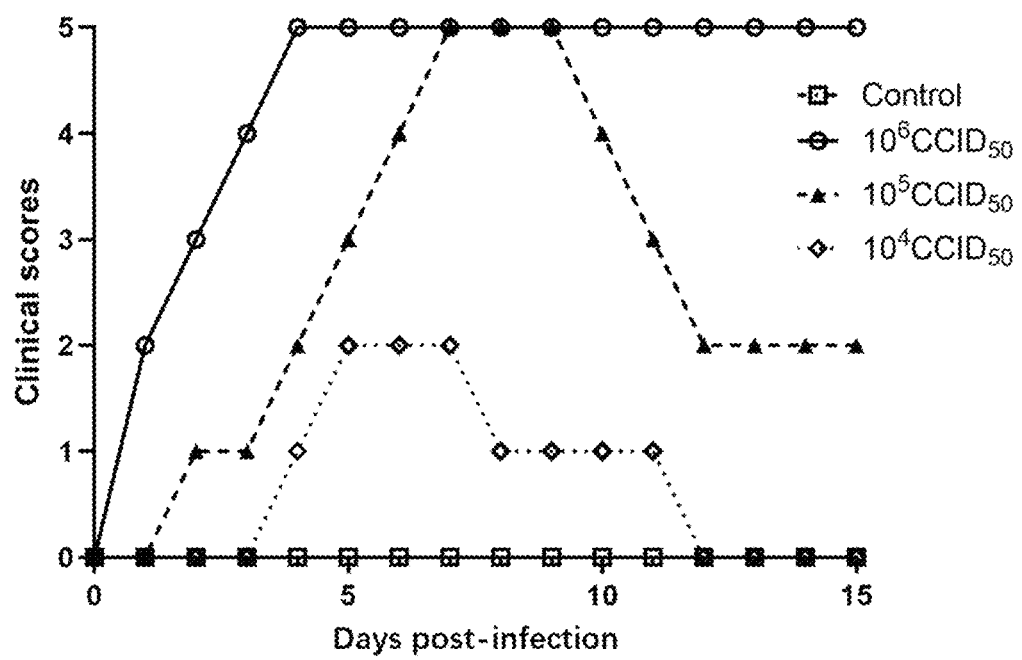
Figure 6A:
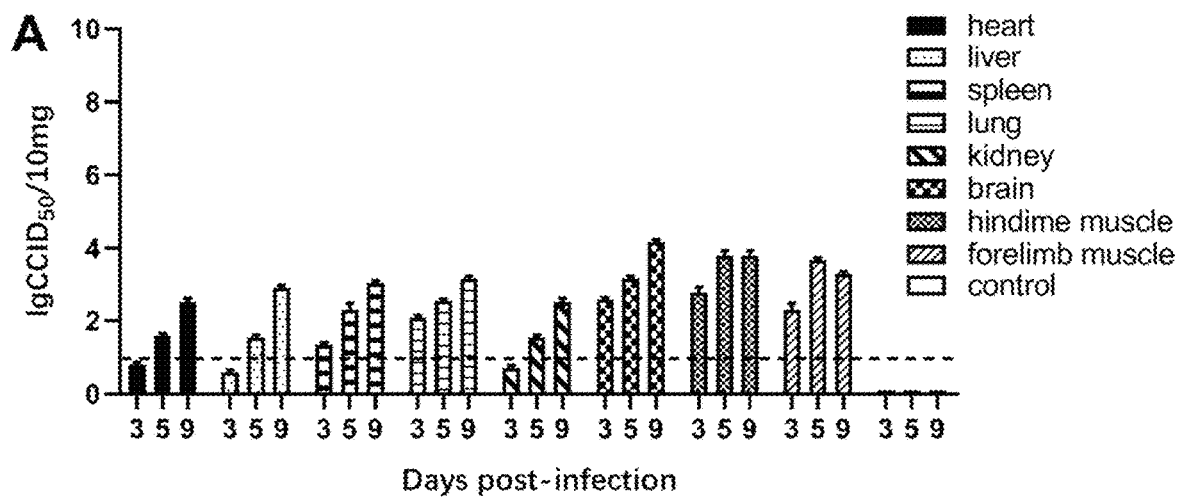
FIG. 6A-FIG. 6C show the changes in viral load in different tissues after inoculation of the CVA6-KM-J33 in 1-day-old suckling mice in Example 5 of the present disclosure; where
Figure 6B:
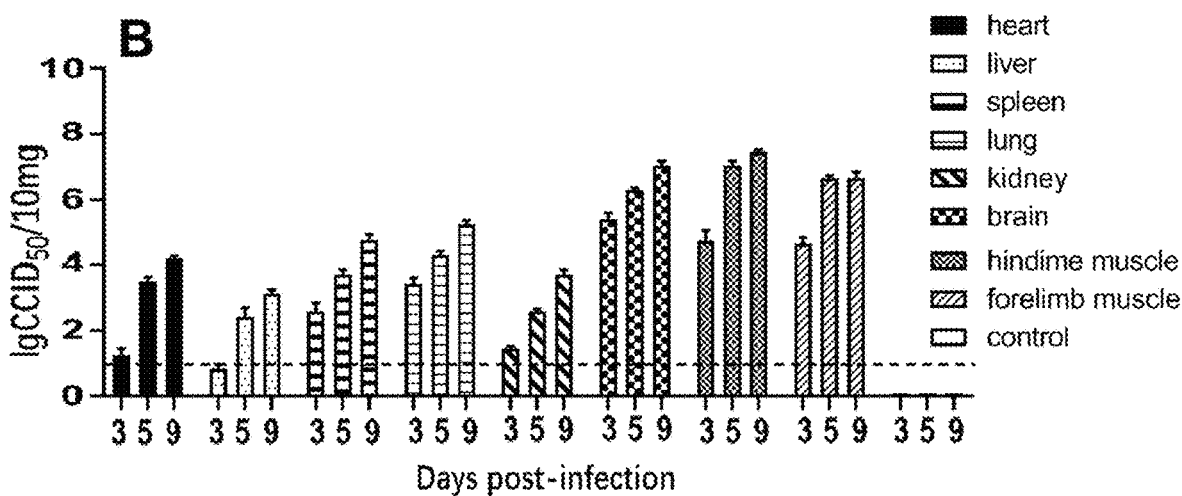
Figure 6C:
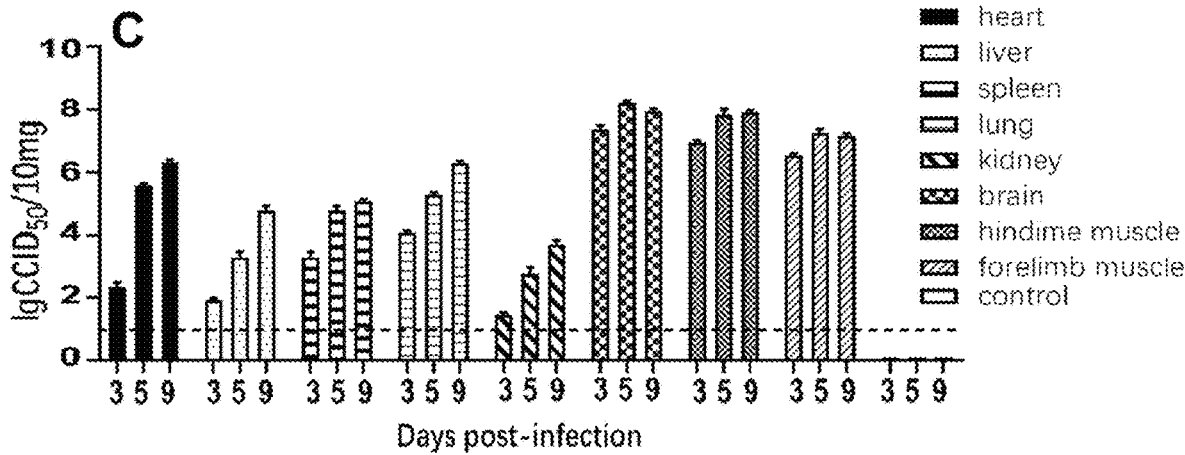
Figure 7A:
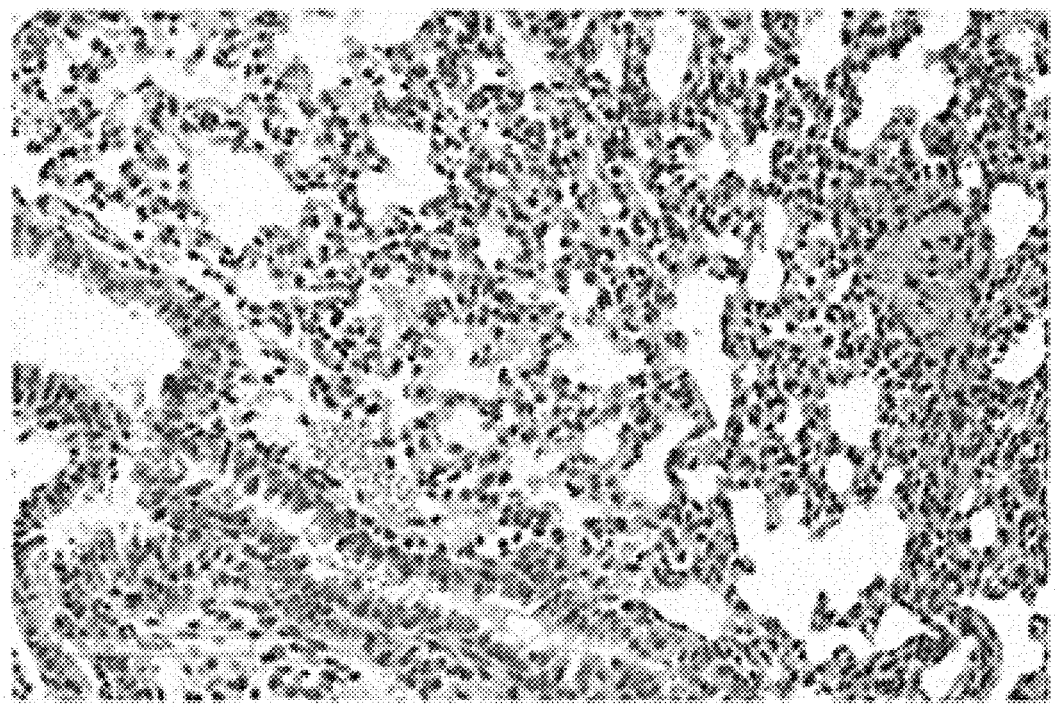
FIG. 7A-FIG. 7D show the H&E staining results of brain and lung tissues of newborn suckling mice infected with the CVA6-KM-J33 in Example 5 of the present disclosure; where
Figure 7B:
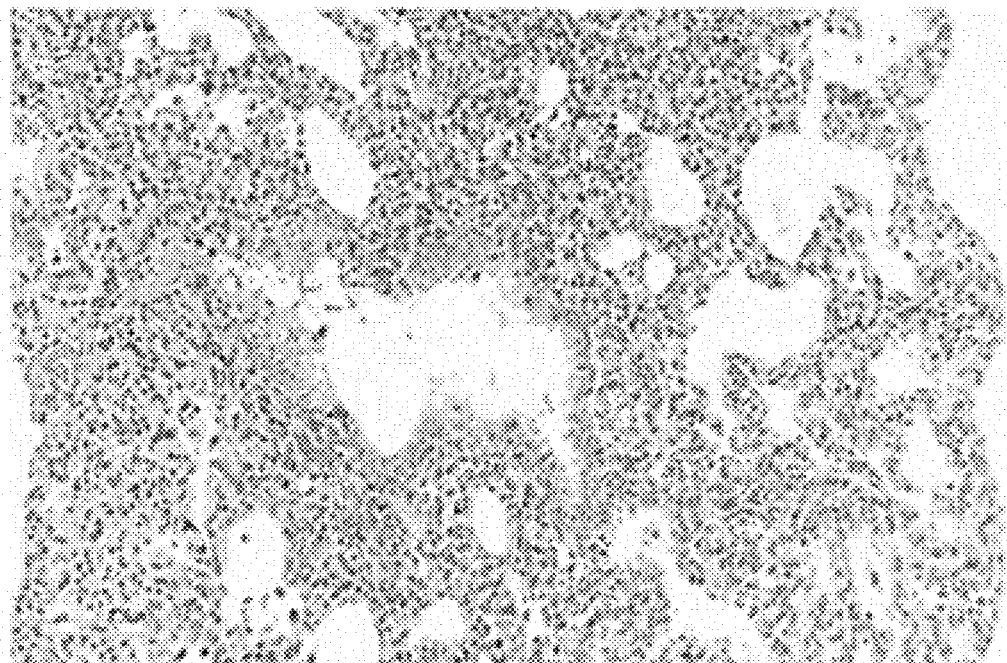
Figure 7C:
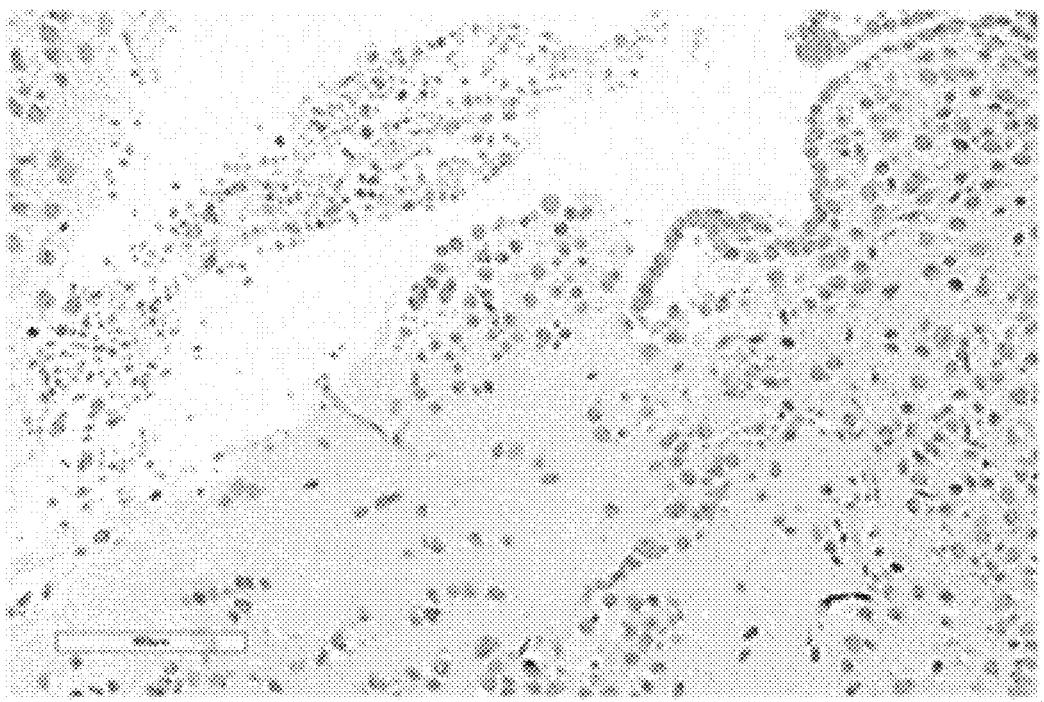
Figure 7D:
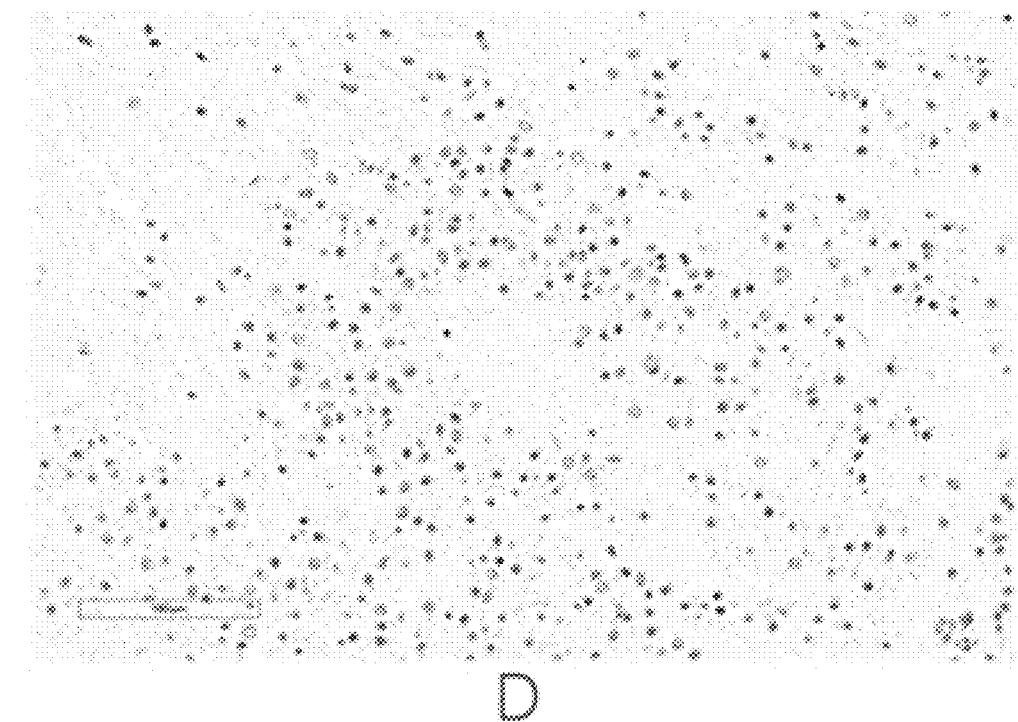

Clinical scores and mortality results are shown in FIG. 5. The CVA6-KM-J33 clone strain amplification solution was used to challenge Balb/c suckling mice at different doses ($10^4$ $CCID_{50}$/mouse, $10^5$ $CCID_{50}$/mouse, and $10^6$ $CCID_{50}$/mouse) via intracerebral injection. The suckling mice in the high-dose group became ill on the 3rd day, where the symptoms of the sick suckling mice were fatigue, hind limb weakness, paralysis of one hind limb, paralysis of both hind limbs, paralysis of the front and rear limbs, and eventually dying or death. All suckling mice died on the 6th day after the challenge. However, the onset time of the suckling mice in the medium and low dose groups was slower, the symptoms of the sick suckling mice did not worsen and the mortality rate was low. Especially in the low-dose group, the symptoms gradually improved 10 days after the challenge and the weight began to increase.

2. Detection of Viral Load in Organs of Suckling Mice Infected with Strain CVA6-KM-J33

In order to study the load and distribution of strain CVA6-KM-J33 in different organs of suckling mice in different stages at different doses, the viral load was measured 3, 5, and 9 days after intracerebral challenge.

Figure 8A:
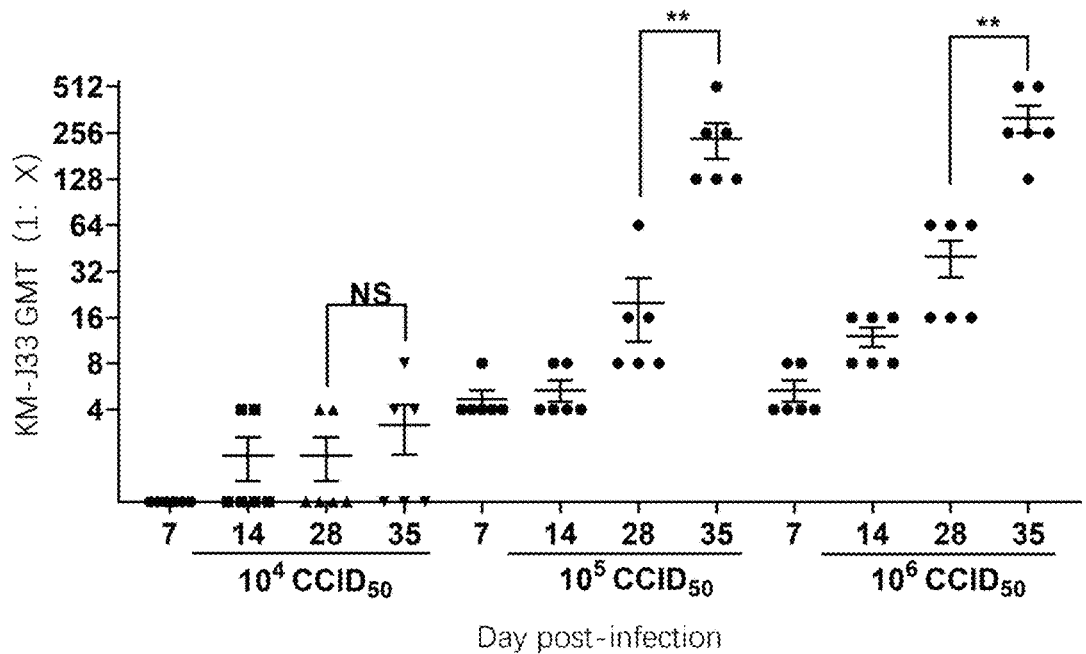
FIG. 8A-FIG. 8B show the immunogenicity evaluation of the experimental inactivated vaccine in Example 6 of the present disclosure, where
Figure 8B:
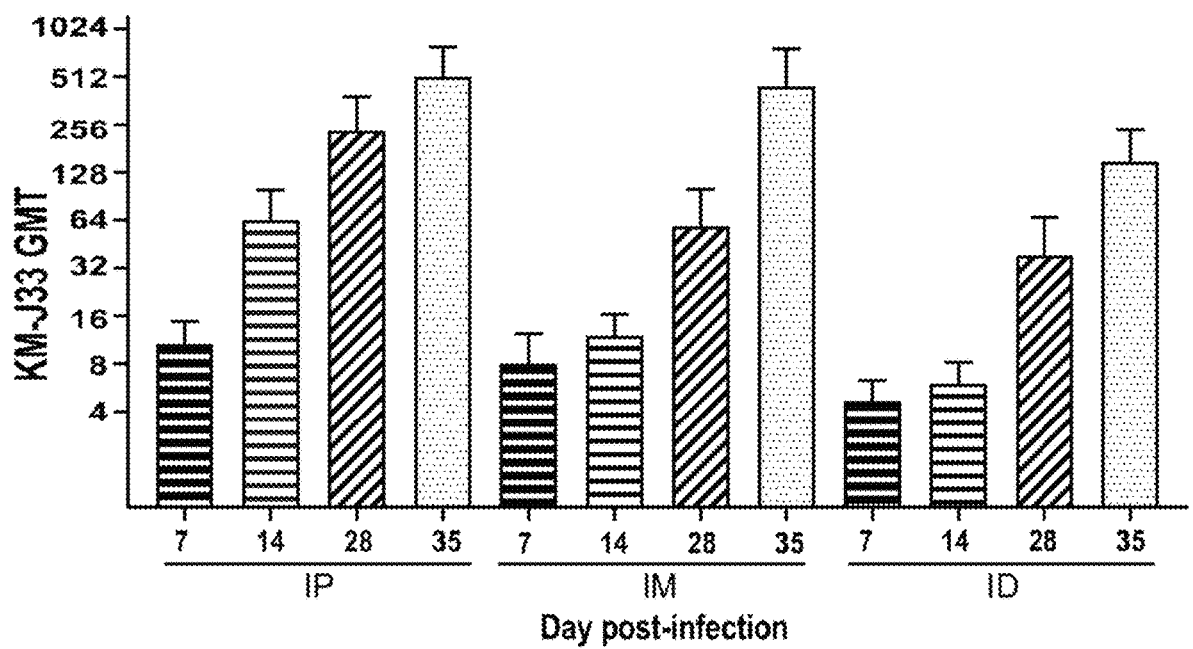

2.1 Preparation of titer standard: CVA6 (CVA6-KM-J33) of known titer (7.0 $lgCCID_{50}$/mL) was selected.

2.2 Extraction of total tissue RNA: 3 infected suckling mice in different dose groups of the intracerebral route were sacrificed on days 3, 5, and 9 after infection, their heart, liver, spleen, lung, kidney, brain, spinal cord, trigeminal nerve, and skeletal muscle where ground thoroughly, 0.01 g of tissue grinds were placed in 1.5 mL sterile centrifuge tubes, added with 0.01 M PBS to 1 mL, centrifuged at 9,000 rpm 4° C. for 10 min, and the supernatant after centrifugation was collected to extract viral nucleic acid by Trizol method to detect the viral load in each tissue.

2.3 qPCR system and reaction conditions: Following the instructions of the One-Step RT qPCR Kit (TAKARA/RR064), 4 μL of template was selected to allow one-step RT qPCR on a fluorescence quantitative PCR instrument (Bio-rad, CFX-96), where a total reaction system was 25 μL. The viral load ($CCID_{50}$/10 mg) in the sample was absolutely quantified based on the standard curve. The qPCR probe and primer sequences, reaction procedures, and systems are shown below.

Primer Sequence

CVA6-qP-F (SEQ ID NO: 7): TACCACCGGGARAAACGTCCACG

CVA6-qP-R (SEQ ID NO: 8): CGGTCAGYTGCAGTGTTAGT

Probe (SEQ ID NO: 9): 5'-FAM-ACGTGAGAGCTTGGGTACMTAGACCCCTTC-BHQ-3'

The reaction system included: 12.5 μL of 2× OnestepRT-PCRbuffer III, 0.5 μL of ExTaqHS, 0.5 μL of PrimeScriptRTEnzymeMixII, 5.5 μL of RNase Free $ddH_2O$, 0.5 μL each of Primer F/R, 1 μL of Probe, and 4 μL of template.

Reaction parameters: 425 min; 9,510 s; 955 s, 6,030 s, 39 cycles.

The experimental results are shown in FIG. 6: the viral load in each organ in the high-dose ($10^6$ $CCID_{50}$/mouse) group showed a significant upward trend on days 3 to 9 after infection; on the 3rd day, the viral loads in the heart, liver, spleen, and kidney were all lower than 5.0 $lgCCID_{50}$/10 mg; on the 9th day after the challenge, the viral load in the heart, spleen, lungs, brain, hind limb muscles, and forelimb muscles of the suckling mice was (6.0-8.5) $lgCCID_{50}$/10 mg. The viral load in each organ in the medium-dose ($10^5$ $CCID_{50}$/mouse) group showed an increasing trend on days 3 to 9 after infection; the viral load in each organ increased on day 3; on the 9th day after infection, the viral load in the heart and skeletal muscles (front and rear limb muscles) of suckling mice could reach (4.0-6.5) $lgCCID_{50}$/10 mg, and the viral load in the brain and skeletal muscles (front and rear limb muscles) was higher than that in other organs. In the low-dose ($10^4$ $CCID_{50}$/mouse) group, there was a gentle upward trend on the 3rd and 5th days after infection, but the changing trend was not obvious on the 9th day.

3. Histopathological Examination of Suckling Mice after Immunization with CVA6 Strain CVA6-KM-J33

Histopathological examination of CVA6-KM-J33-immunized suckling mice: the pathology of the brain and lung tissues of suckling mice was observed, and organs were fixated in 10% neutral formalin for 48 h and then embedded in paraffin to make paraffin sections for H&E staining.

CVA6-KM-J33 intracerebral route: 1-day-old SPF grade Balb/c suckling mice infected at a dose of $10^6$ $CCID_{50}$/mouse were sacrificed, and brain and muscle (forelimbs and hindlimbs) tissues of the diseased suckling mice and the healthy suckling mice of the control group were collected on the 9th day after infection for histopathology. The H&E staining results are shown in FIG. 7. It was found that in the late stage of infection, damages, and inflammatory reactions occurred in multiple organs throughout the body, such as perivascular infiltration of inflammatory cells, tissue congestion, and inflammatory cell accumulation. The changes in these cases showed a gradual worsening trend as time progressed. Brain: the pathological examination showed obvious pathological changes in the brain, local focal hemorrhage, local meningeal and subarachnoid congestion and hemorrhage, fewer neurons in the brain, mild edema, and pyknosis of individual cell nuclei. No obvious pathological changes were found in negative control brain tissue sections. Lung: the H&E staining had found that infection of suckling mice with CVA6-KM-J33 could cause viral pneumonia in suckling mice, manifested by congestion, mild degeneration, and thickening of blood vessel walls; while there were cell proliferation, mild expansion of tracheal alveoli, and endothelial cell necrosis and shedding; and a small number of red blood cells, exfoliated tissue cells, and inflammatory cells were seen in the alveolar spaces and some bronchioles. No obvious pathological changes were found in negative control lung tissue sections.

Example 6 Immunogenicity Evaluation of Strain CVA6-KM-J33

In order to explore the immune dose of CVA6-KM-J33 and the impact of different immune routes on the immune effect of CVA6-KM-J33, 3 immune routes of muscle, abdominal cavity, and intradermal were set up, and vaccination doses were: 9 different combinations of $10^4$ $CCID_{50}$/mouse, $10^5$ $CCID_{50}$/mouse, and $10^6$ $CCID_{50}$/mouse were used to immunize 6-week-old Balb/c mice.

The serum antibody titer test results showed that the neutralizing antibody seroconversion rates of mice in the 9 experimental groups on the 7th day after primary immunization were all lower than 50% (1:8 was regarded as a threshold for vaccine efficacy evaluation). As the days after infection increased, the serum neutralizing antibody seroconversion rates of mice in the medium-dose group and the high-dose group increased; on the 28th day after the primary immunization, the positive conversion rates of the intramuscular low-dose group, intraperitoneal low-dose group, intradermal low-dose group, and intramuscular medium-dose group were less than 100%, while the positive conversion rates of the other experimental groups all reached 100%. A booster immunization was carried out on the 28th day. On the 7th day after the booster immunization, except for the intramuscular low-dose group, intraperitoneal low-dose group, and intradermal low-dose group, the antibody-positive conversion rate of each experimental group increased to 100% (FIG. 8).

Statistical analysis of the data showed that there was no statistically significant difference in the data of the muscle, intraperitoneal, and intradermal route immune groups in different dose groups (t=0.216, p=0.892), such that the data of the 9 experimental groups could be combined and analyzed. From the perspective of immunization time points, except for the low-dose group, the antibody levels of mice on the 7th day after booster immunization were significantly higher than those on the 28th day after the primary immunization (FIG. 8); from the perspective of different immune routes, intradermal, intramuscular, and intradermal routes all produce immune effects, but the intramuscular and intraperitoneal routes had better immune effects. The highest antibody titer after immunizing mice was 1:1024, and the highest antibody titer in mice immunized via intradermal route was 1:256. (FIG. 8). The above results suggested that CVA6-KM-J33 in the medium-dose group with $10^6$ CCID$_{50}$/animal and the high-dose group with $10^7$ CCID$_{50}$/animal had desirable immunogenicity, indicating that the CVA6-KM-J33 could produce higher titer antibodies in the mouse serum after immunizing Balb/c mice through the intraperitoneal and intramuscular routes.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. A method for propagating and passaging the CVA6 strain CVA6-KM-J33 comprising infecting a human embryonic lung diploid cell with a Coxsackievirus A6 (CVA6) strain CVA6-KM-J33 and culturing the human embryonic lung diploid cell at 37° C. under 5% $CO_2$;

wherein the human embryonic lung diploid cell is a KMB17 human embryonic lung diploid cell; and wherein the CVA6 strain CVA6-KM-J33 has a deposit number of CCTCC NO. V202384 in the China Center for Type Culture Collection and a VP1 structural protein of the CVA6 strain CVA6-KM-J33 has the amino acid sequence set forth in SEQ ID NO: 10.

* * * * *